US012718911B2

(12) United States Patent
Shrivastava et al.

(10) Patent No.: US 12,718,911 B2
(45) Date of Patent: Aug. 25, 2026

(54) QUERYING AND ANALYSIS OF CLINICAL TRIALS USING PROBABILISTIC GRAPHICAL MODELS

(71) Applicant: Microsoft Technology Licensing, LLC, Redmond, WA (US)

(72) Inventors: Harsh Shrivastava, Redmond, WA (US); Urszula Stefania Chajewska, Issaquah, WA (US); Muhammad Arrabi, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 193 days.

(21) Appl. No.: 18/500,834

(22) Filed: Nov. 2, 2023

(65) Prior Publication Data

US 2025/0149128 A1 May 8, 2025

(51) Int. Cl.
*G16H 10/20* (2018.01)
*G16H 50/20* (2018.01)

(52) U.S. Cl.
CPC ............ *G16H 10/20* (2018.01); *G16H 50/20* (2018.01)

(58) Field of Classification Search
None
See application file for complete search history.

(56) References Cited

U.S. PATENT DOCUMENTS 11,626,189 B2 * 4/2023 DeMeyer .............. G06Q 50/22 705/2
2010/0125241 A1 * 5/2010 Prud'Homme ........ G16H 20/17 600/300
2020/0251188 A1 * 8/2020 Will ....................... G16H 10/60
2022/0172091 A1 * 6/2022 Wasserkrug ............. G06N 7/01
2023/0238087 A1 * 7/2023 Jain ........................ G16H 50/20 705/2
2023/0298707 A1 * 9/2023 Gray ..................... G06F 40/295 705/2
2024/0404699 A1 * 12/2024 Yamazaki .............. G16H 30/40
2025/0094824 A1 * 3/2025 Shrivastava ........... G06N 3/042

FOREIGN PATENT DOCUMENTS

CA 3220786 A1 * 12/2022 ........... G06F 16/906
WO WO-2020254291 A1 * 12/2020 ......... G06F 18/2193
WO WO-2022018771 A1 * 1/2022 ............ G16H 50/30
WO WO-2023039111 A1 * 3/2023 ............ G16H 10/20
WO WO-2025085632 A1 * 4/2025 ............ G16H 10/20

OTHER PUBLICATIONS

Belhadi, A., Djenouri, Y., Diaz, V. G., Houssein, E. H., & Lin, J. C.-W. (2022). Hybrid intelligent framework for automated medical learning. Expert Systems, 39(6), e12737. (Year: 2022).*

* cited by examiner

*Primary Examiner* — Robert A Sorey
(74) *Attorney, Agent, or Firm* — Ray Quinney & Nebeker P.C.; Tiffany B. Healy

(57) ABSTRACT

The present disclosure relates to methods and systems that provide querying and analysis of clinical trials using probabilistic graphical models. The methods and systems train a probabilistic graphical model using clinical trial data and use the probabilistic graphical model to perform inferences in response to queries for clinical trials. The methods and systems use the probabilistic graphical model to handle multimodal datatypes of the clinical trial data and predict multiple attributes of the clinical trial for an input query.

18 Claims, 5 Drawing Sheets

QUERYING AND ANALYSIS OF CLINICAL TRIALS USING PROBABILISTIC GRAPHICAL MODELS

BACKGROUND

Clinical trials are used to design new drugs, design new treatments for diseases, and improve patient monitoring. Each clinical trial conducted follows a particular structure of gathering and recording the clinical trial data. For instance, with each clinical trial, there is an associated set of inclusion criteria, a set of exclusion criteria, number of participants, the disease targeted, evaluation protocol and other such fields. Often, when researchers are designing a new trial, they are faced with the problem of determining the values of these fields. These values depend on clinical trial's goals, rarity of the disease in question, expected effect size, and the budget. The researchers take clues of closely related trials to determine field values. For example, if a particular trial is aiming for understanding some pregnancy related complications and they are debating on the number of participants to consider. Then, one approach taken by the researchers can be to sought trials that have studied pregnant participants for a related complication and make their decision based on the number of participants in the related studies.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Some implementations relate to a method. The method includes training a probabilistic graphical model using clinical trial data, wherein the probabilistic graphical model represents a distribution over a domain of the clinical trial data. The method includes receiving a query for a new clinical trial. The method includes using the probabilistic graphical model to perform inference tasks in response to the query. The method includes providing an output of the inference tasks as a response to the query.

Some implementations relate to a device. The device includes a processor; memory in electronic communication with the processor; and instructions stored in the memory, the instructions being executable by the processor to: train a probabilistic graphical model using clinical trial data, wherein the probabilistic graphical model represents a distribution over a domain of the clinical trial data; receive a query for a new clinical trial; use the probabilistic graphical model to perform inference tasks in response to the query; and provide an output of the inference tasks as a response to the query.

Additional features and advantages will be set forth in the description which follows, and in part will be obvious from the description, or may be learned by the practice of the teachings herein. Features and advantages of the disclosure may be realized and obtained by means of the instruments and combinations particularly pointed out in the appended claims. Features of the present disclosure will become more fully apparent from the following description and appended claims or may be learned by the practice of the disclosure as set forth hereinafter.

BRIEF DESCRIPTION OF THE DRAWINGS

In order to describe the manner in which the above-recited and other features of the disclosure can be obtained, a more particular description will be rendered by reference to specific implementations thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example implementations, the implementations will be described and explained with additional specificity and detail through the use of the accompanying drawings in which.

DETAILED DESCRIPTION

Figure 1:
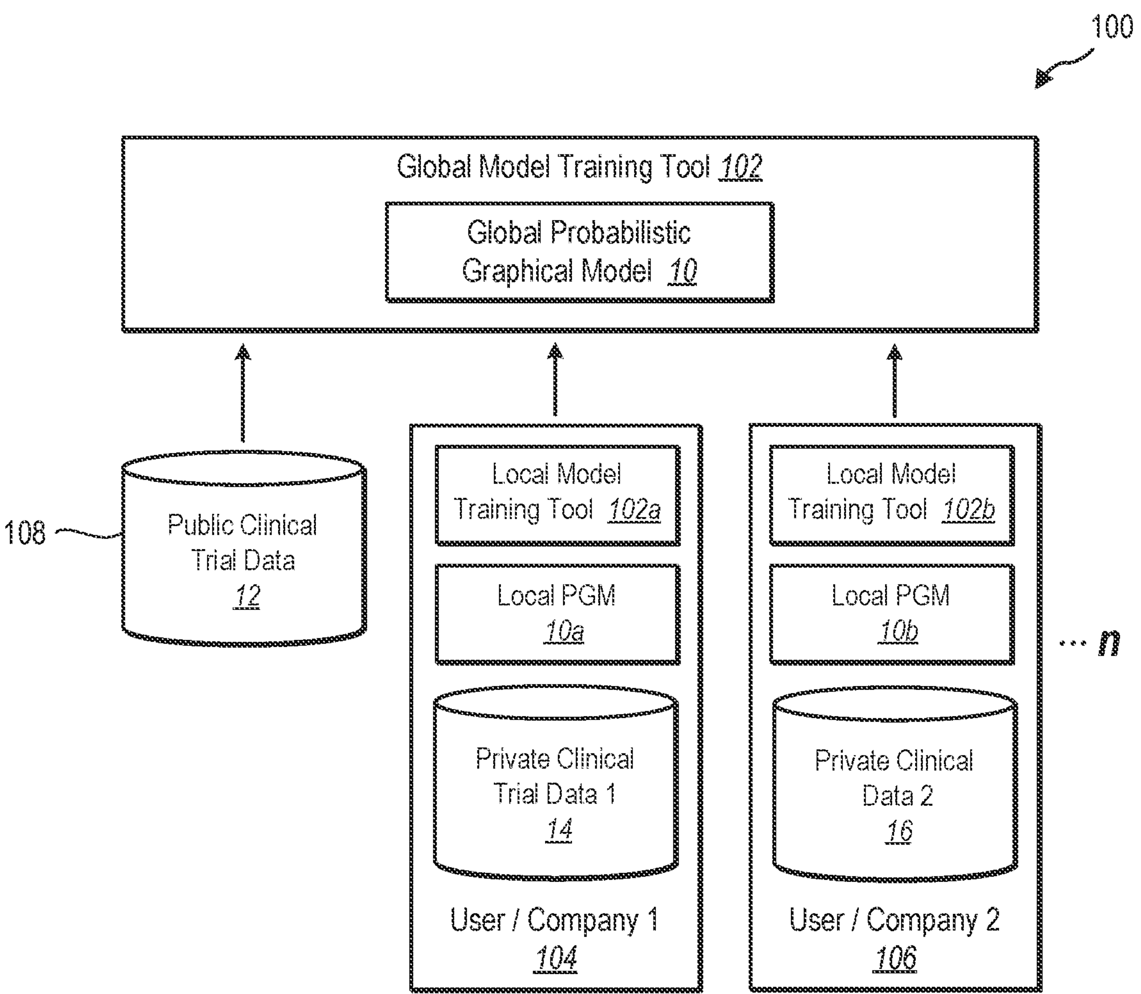
FIG. 1 illustrates an example environment for training a probabilistic graphical model using clinical trial data in accordance with implementations of the present disclosure.

This disclosure generally relates to querying and analysis of clinical trials using probabilistic graphical models. Clinical trials explore the safety and efficacy of medical interventions: drugs, procedures, devices and treatments. Clinical trials are run as randomized controlled experiments with treatment group(s) and control group(s) with carefully screened participants. A detailed evaluation and comparison between groups (often including also subgroups) is performed at the end. Clinical trials proceed in three phases, moving to the next phase usually requires an FDA (or analogous agency) approval. There are publicly available databases of privately and publicly funded clinical studies conducted around the world. However, majority of clinical trials conducted are not reported to the publicly available databases. Large pharmaceutical companies which sponsor tens and hundreds of clinical trials may have trial data not yet reported or databases with more detailed trial data than officially available in the publicly available databases.

Each clinical trial conducted follows a particular structure of gathering and recording the clinical trial data. For instance, with each clinical trial, there is an associated inclusion criteria, exclusion criteria, number of participants, the disease targeted and other such fields. Clinical trials may take years to complete and cost a significant amount of money to conduct. If the clinical trial fails to complete, or fails to provide a result, the company that designed the clinical trial may have spent a significant amount of money without receiving the desired information from the clinical trial.

When researchers are designing a new trial, they are faced with the problem of determining the values of the fields of the clinical trial. When designing a new clinical trial, there are numerous design decisions the researchers are making for the clinical trials. For example, the researchers are deciding what tests will be performed, a frequency of tests performed, a number of centers to participate in the clinical trial, a number of volunteers to recruit for the clinical trial, and/or criteria for the volunteers recruited for the clinical trials (e.g., age, presence or absence of certain medical conditions diagnosed in the volunteers, etc.). Each clinical trial has different attributes and choices in the values for the different attributes can significantly affect whether the clinical trial completes or whether the clinical trial fails to complete. When designing a new clinical trial, researchers are attempting to make design decisions to prevent the clinical trial from failing (e.g., the clinical trial fails to complete, not enough volunteers were recruited, or volunteers stop participating before the end of the clinical trial, the effect of the treatment in question was present, but the effect size didn't reach statistical significance).

The researchers typically take clues of closely related trials (e.g., from publicly available databases of clinical trial information) to determine field values. For example, if a particular trial is aiming for understanding some pregnancy related complications and they are debating on the number of participants to recruit. One approach taken by the researchers can be to find trials that have studied pregnant participants for a related complication and make their decision based on the number of participants in the related studies.

The present disclosure provides methods and systems for aiding users in making design decisions for clinical trials. The methods and systems allow the users to perform counterfactual reasoning for designing clinical trials to aid the user in understanding how modifying different criteria of the clinical trial may affect a success of a clinical trial. A clinical trial may be successful if the clinical trial manages to recruit a sufficient number of volunteers. A clinical trial may be successful if the clinical trial finishes. A clinical trial may be successful if the clinical trial provides information the company uses for the drug or drug treatment. The present disclosure includes a number of practical applications that provide benefits and/or solve problems associated with querying and analysis of clinical trials using probabilistic graphical models. Examples of these applications and benefits are discussed in further detail below.

The systems and methods of the present disclosure provide a Probabilistic Graphical Model (PGM) approach that answers conditional queries of users for different fields related to a description of a clinical study. Probabilistic graphical models are used to capture highly non-linear dependencies to learn the underlying distribution from the existing set of clinical studies available. Since, the clinical trials data is structured in a specific format, the Bayesian networks, Markov networks, and deep neural network based PGM representations (e.g., Neural Graphical Models) used by the systems and methods are designed to adhere to the structure of clinical trials data. The methods and systems model variables based on data from past clinical trials and connections that are not explicitly included in the clinical trial data. For example, the clinical trial data can be accessed from public websites, such as, clinicaltrials.gov.

By using probabilistic graphical models, the methods and systems allow the users to perform counterfactual reasoning over the clinical trials data. In some implementations, the users set different variable(s) of interest for the new clinical trials, or existing clinical trials, and the methods and systems provide maximum a-posteriori values for all the other clinical trial attributes given specific values of variable(s) of interest. In some implementations, the users provide different values for the attribute(s) of the clinical trial and the methods and systems provide an output with a probability distribution over the remaining attributes conditioned on provided values. For example, the methods and systems may provide an output with a probability distribution over the variable indicating the clinical trial completing. Another example includes the methods and systems providing an output with a probability distribution over the variable representing recruiting enough volunteers for the clinical study.

Learning, inference, and sampling are operations that make probabilistic graphical models useful for domain exploration. Learning, in a broad sense, consists of fitting the distribution function parameters from data. Inference is the procedure of answering queries in the form of marginal distributions or reporting conditional distributions with one or more observed variables. Sampling is the ability to draw samples from the distribution defined by the probabilistic graphical model.

In some implementations, the probabilistic graphical models are Neural Graphical Models that learn the underlying distribution from the existing set of clinical studies available. Neural Graphical Models are probabilistic graphical models that utilize the expressive power of neural networks to learn complex non-linear dependencies between the input attributes. Neural Graphical Models learn to capture the underlying data distribution and have efficient algorithms for inference and sampling.

Neural Graphical Models are a type of probabilistic graphical model that handle complex distributions over a domain and represents a richer set of distributions as compared to traditional probabilistic graphical models. Neural Graphical Models remove the restrictions previously placed over a domain by traditional probabilistic graphical models. Neural Graphical Models represent complex distributions without restrictions on the domains or predefined assumptions about the domains and may capture high distributions defined by the data for a domain.

Neural Graphical Models accept a feature dependency structure that can be given by an expert or learned from data. The dependency structure may have the form of a graph with clearly defined semantics (e.g., a Bayesian network graph or a Markov network graph) or an adjacency matrix. In some implementations, the feature dependency structure is an attribute graph based on the clinical trial data. The graph may be either directed or undirected. Based on this dependency structure, Neural Graphical Models represent the joint probability distribution over the domain by using expressive power of deep neural networks. The parameterization of such a network can be learned from data efficiently, with a loss function that jointly optimizes adherence to the given dependency structure and fit to the data. Probability functions represented by Neural Graphical Models are unrestricted by any of the common restrictions inherent in other probabilistic graphical models.

The Neural Graphical Models represents the functions of the different features using a neural network. The neural network represents the distribution(s) over the domain. The neural network is a deep learning architecture with hidden layers. The functions represented using the neural network capture the dependencies identified in the dependency structure. The functions are represented in the neural network by the paths from nodes in the input layer through the neural network hidden layer(s) to the node in the output layer. Thus, as the number of neural network layers increases in the neural view and/or the number of units in each hidden layer increase, the complexity of the functions represented by the neural view increases. The Neural Graphical Models represent complex distributions over features of a domain. A domain is a complex system that is being modeled (e.g., a disease process or a clinical trial).

Neural Graphical Models learn the underlying probability distribution from multimodal data (e.g., text, images, continuous, categorical, etc.). The Neural Graphical Model has the ability to model with multimodal input data types and may capture any type of data for the domain. Moreover, Neural Graphical Models inference capabilities allow efficient calculation of conditional and marginal probabilities which can answer many complex queries.

In some implementations, the methods and systems use federated learning to generate a global Neural Graphical Model based on a plurality of trained Neural Graphical Models. One of the benefits of pooling all clinical trial data is to obtain more accurate assessment of clinical trial success rates for each phase and provide insight into features with most impact on that success and provide more accurate models for everyone to use in the inference and sampling tasks. The methods and systems may use the global Neural Graphical Models to provide answers to user's queries related to designing new clinical trials. In some implementations, the methods and systems create personalized global Neural Graphical Models based on the private clinical trial data of a user and use the personalized global Neural Graphical Models to provide answers to user's queries related to designing new clinical trials.

One technical advantage of the systems and methods of the present disclosure is ability to handle multimodal data. Another technical advantage of the systems and methods of the present disclosure is graph structure discovery of the underlying connections within the domain. Another technical advantage of the systems and methods of the present disclosure is supporting prediction of multiple fields of clinical studies. In some implementations, the response can be conditioned on multiple input fields. Another technical advantage of the systems and methods of the present disclosure is learning an underlying distribution of augmented clinical trial data which can model external variables together with variables recorded in clinical trial database.

The methods and systems of the present disclosure allow users (e.g., the new clinical trial designers) to create better trial designs by providing a clinical trial tool the users can use to get answers to questions about the new clinical trial design and vary different attributes values of the new clinical trial design to get responses from the clinical trial tool indicating trial's outcome variables' dependence on these attribute values. It allows the users to design a successful new clinical trial and make the new clinical trial cost effective and efficient. The users may repeatedly provide questions about the new clinical trial design to the clinical trial tool varying different attributes and/or values of the different attributes and receiving responses from the clinical trial tool in the form of a probability distribution over the variable representing clinical trial completion (or other outcome variables) with the different attributes and/or values provided. The users may also perform counterfactual reasoning using the clinical trial tool and provide different variable(s) of interest for the new clinical trial design and receive responses from the clinical trial tool with maximum a-posteriori values for all other attributes most likely to achieve the desired values of the variable(s) of interest.

Referring now to FIG. 1, illustrated is an example environment 100 for training a probabilistic graphical model 10 using clinical trial data. The environment 100 includes a model training tool 102 that trains a probabilistic graphical model 10 using clinical trial data. The probabilistic graphical model 10 is trained using clinical trial data from the existing set of clinical studies available. The probabilistic graphical model 10 is used to capture highly non-linear dependencies to learn the underlying distribution from the clinical trial data. A probabilistic graphical model is a probabilistic model for which a graph expresses the conditional dependence structure between random variables. Probabilistic graphical models use a graph-based representation as the foundation for encoding a distribution over a multi-dimensional space and a graph that is a compact or factorized representation of a set of independencies that hold in the specific distribution.

In some implementations, the model training tool 102 trains the probabilistic graphical model 10 using public clinical trial data 12. Public clinical trial data 12 is available through publicly accessible datastores 108. For example, the public clinical trial data 12 accessed from public websites, such as, clinicaltrials.gov. In some implementations, the model training tool 102 is a global model training tool that is publicly accessible (or accessible to all users 104, 106) that uses the public clinical trial data 12 to train the probabilistic graphical model 10.

In some implementations, the model training tool 102 is a local model training tool 102*a* local to the user 104 or a local model training tool 102*b* that is local to the user 106 and trains the probabilistic graphical model 10 using private clinical trial data of the users' 104, 106. Private clinical trial data is available to select individuals or organizations in datastores controlled by a private organization (e.g., a user, a company, and/or university). For example, the user 104 has private clinical trial data 14 and the local model training tool 102*a* trains a local probabilistic graphical model 10*a* using the private clinical trial data 14 of the user 104. Another example includes the user 106 has private clinical trial data 16 and the local model training tool 102*b* trains a local probabilistic graphical model 10*b* using the private clinical trial data 16 of the user 106. In some implementations, the local model training tool 102*a* trains the local probabilistic graphical models 10*a* using a combination of public clinical trial data 12 and the private clinical trial data 14 and the local model training tool 102*b* trains the local probabilistic graphical model 10*b* using a combination of public clinical trial data 12 and the private clinical trial data 16.

In some implementations, the knowledge from a plurality of datastores (up to n, where n is a positive integer) may be used by the model training tool 102 for training a probabilistic graphical model 10 using the federated learning framework without obtaining the private clinical trial data (e.g., the private clinical trial data 14, 16).

The training of the probabilistic graphical model 10 starts with selecting data domain and the representation of the clinical trial data. For example, the model training tool 102 determines whether to use all of the clinical trial data to train one probabilistic graphical model 10 or use a set of subsets of the clinical trial data to train multiple probabilistic graphical models 10 (e.g., different probabilistic graphical models 10 for clinical trials focusing on different drugs or diseases). For example, one probabilistic graphical model 10 is used for clinical trials focusing on diabetes and a different probabilistic graphical model 10 is used for clinical trials focusing on drugs for heart attacks.

The model training tool 102 determines which attributes and/or subcategories of the attributes of a clinical trial to include in the training data. Example attributes include participation criteria, study plan, study overview, contacts and locations, collaborators and investigators, intervention/treatment, enrollment numbers of participants, study type, location of the centers, eligibility criteria, inclusion criteria, exclusion criteria, evaluation protocols, and/or outcome measures. Example subcategories of attributes include ages eligible for the study, sexes eligible for the study, specific health conditions and diagnoses to require of participants in the study, specific health conditions that would prevent participants from being eligible from the study, intervention/treatment steps, secondary outcome measures, allocation methods, and/or masking requirements.

The clinical trial data is structured in a specific format. Each clinical trial follows the specific format with different sections of the clinical trial. The sections include but are not limited to: the study overview, disease target, treatment options, contacts and locations, participation criteria, study plan, evaluation protocol, outcome metrics, collaborators and investigators, publications, and study record dates. Bayesian networks, Markov networks, as well as deep neural network representations (e.g., Neural Graphical Models), can be used as the probabilistic graphical model 10. They are trained to adhere to the structure of clinical trials data. The probabilistic graphical model 10 models use variables from the clinical trial data to model connections that are not explicitly represented in the clinical trial data. In some implementations, the nodes of the probabilistic graphical model 10 are different attributes of the clinical trials. Example attributes of the clinical trials include number of participants of a clinical trial, inclusion criteria, exclusion criteria, number of centers for the clinical trial, a disease the clinical trial focuses on, and/or a drug/treatment being tested by the clinical trial.

Each clinical trial has different attributes and different values for the attributes for the sections of the clinical trials. In some implementations, the probabilistic graphical model 10 uses embeddings to model the different attributes in the nodes of the probabilistic graphical model 10. Embeddings are vector representations of entities. The embeddings abstract details from the attributes and capture the essence of the attributes from the different clinical trials. In the clinical trial case, embeddings are particularly useful to model clinical trial data sections with varying sets of attributes for different clinical trials.

The probabilistic graphical model 10 also uses embeddings to handle multimodal data types. For example, the model training tool 102 creates embeddings for each section of the clinical trials (e.g., an embedding for the study overview section, an embedding for the contacts and locations section, an embedding for the participation criteria section, an embedding for the study plan section, an embedding for the collaborators and investigators section, an embedding for the publications section, an embedding for the study record dates). Another example includes the model training tool 102 creates embeddings for the different subsections of each section of the clinical trials (e.g., an embedding for the inclusion criteria, an embedding for the exclusion criteria, an embedding for the observation model, an embedding for the study population, an embedding for the sampling method, etc.).

The embeddings of sections and subsections of the clinical trial data (the public clinical trial data 12 and/or the private clinical trial data 14, 16) are used as input to the probabilistic graphical model 10. For example, the embeddings are created from the public clinical trial data 12 and the private clinical trial data 14 or the private clinical trial data 16.

The model training tool 102 may identify any number of attributes to include in the probabilistic graphical model 10 as nodes, or, in the case of embeddings, hypernodes. In some implementations, the probabilistic graphical model 10 is automatically learned by the model training tool 102 using the clinical trial data. For example, the model training tool 102 uses a machine learning algorithm to automatically learn the probabilistic graphical model 10. The nodes of the probabilistic graphical model 10 are the attributes of the clinical trial (e.g., the inclusion criteria, outcome measures, exclusion criteria, dosage requirements, drug being studied, treatment plans, etc.) In the graph associated with the probabilistic graphical model 10 the edges indicate direct node (variable) dependencies. An absence of an edge between nodes (variables) $x_i$ and $x_j$ indicates that $x_i$ and $x_j$ are conditionally independent of each other given other variables.

In some implementations, the model training tool 102 trains the probabilistic graphical model 10 using augmented data. The data may be augmented by bringing in external sources of information, other than clinical trial data. The first step in training the probabilistic graphical model 10 using augmented data may involve creating an augmented attribute graph 24. The augmented attribute graph 24 connects different attributes of a collection of clinical trials. In some implementations, a user provides the data used to augment the dataset. In some implementations, the augmented attribute graph 24 is automatically learned by algorithms based on the augmented dataset. One example augmented data is a data including drug drug side effects graph. Another example augmented dataset is data including protein protein interactions. As an example, consider a clinical trial that was aiming to target a protein "P1." There may be a set of proteins found related to the protein "P1" illustrated in a protein-protein interaction (PPI) graph, e.g., Pc=[P2, P3, P4 . . . ]. The set of additional proteins "Pc" may be added as an attribute to the clinical trials data.

The model training tool 102 trains the probabilistic graphical model 10 using the clinical trial data. In some implementations, the model training tool 102 trains the probabilistic graphical model 10 using the samples and embedding representations from multiple clinical trials obtained from the public clinical trial data 12. In some implementations, the model training tool 102 trains the probabilistic graphical model 10 using samples and embedding representations from multiple clinical trials obtained from the public clinical trial data 12 and the private clinical trial data. For example, model training tool 102 running within the user 104 environment obtains the private clinical trial data 14 from a datastore of the user 104. Another example includes the model training tool 102 running within the user 106 environment obtains the private clinical trial data 16 from a datastore of the user 106 but is unable to access the private clinical trial data 14 from the datastore of the user 104 because the user 106 is unauthorized to access the private clinical trial data 14 of the user 104.

In some implementations, the clinical trial tool 110 uses the clinical trial data to train a Neural Graphical Model 26. A Neural Graphical Model is a type of probabilistic graphical model implemented using a deep neural network that handles complex distributions over a domain. A domain is a complex system that is being modeled (e.g., clinical trials, or a disease process). The Neural Graphical Model 26 represents complex distributions over the domain without restrictions on the domain or predefined assumptions of the domain. In some implementations, the Neural Graphical Model 26 is trained on all clinical trials covering different diseases. In some implementations, the Neural Graphical Model 26 is trained for different diseases (e.g., one Neural Graphical Model 26 is trained for cancer and another Neural Graphical Model 26 is trained for diabetes).

The Neural Graphical Model 26 can model with multimodal input data types (e.g., text, images, continuous, categorical, etc.) and contexts of data and may capture any type of data for the domain. In some implementations, the clinical trial data is multimodal data that spans different types of data (e.g., text, images, continuous, categorical, etc.).

In some implementations, the global model training tool 102 uses a federated learning framework to train a Neural Graphical Model using the public clinical trial data 12 and the separate local models trained on private clinical trial data 14, 16 of each user 104, 106. Each user 104, 106 shares the models trained on private clinical trial data 14, 16 of the users' 104, 106 with the model training tool 102. The federated learning framework combines the knowledge gained from private clinical trial data 14, 16 without having access to the private clinical trial data 14, 16 to train a Global Neural Graphical Model.

The Global Neural Graphical Model covers the common feature sets and the union of value sets across the private clinical trial data 14, 16 of the users 104, 106. The Global Neural Graphical Model 28 allows the users 104, 106 to benefit from the diverse datasets from the users 104, 106 while keeping the clinical trial data private to the users' 104, 106. The Global Neural Graphical Model 28 pools the knowledge gained from clinical trial data (the private clinical trial data 14 of the user 104 and the private clinical trial data 16 of the user 106 with the public clinical trial data 12) without having access to private data and learns the underlying data distribution while the private clinical trial data 14, 16 is kept within the users' 104, 106 environments. In some implementations, the model training tool 102 ensures that the global Neural Graphical Model shared with users is based on no less than k (where k is a positive integer) users private clinical trial data. The value for k may be determined based on the sensitivity of the clinical trial data. For example, k may be a higher number for sensitive data that must remain private (e.g., sensitive patient information). One of the benefits of pooling the knowledge gained from private clinical trial data from the users 104, 106 is to obtain more accurate assessment of clinical trial success rates for each phase and provide insight into features with most impact on that success and provide more accurate models for everyone to use in the inference and sampling tasks for clinical trials.

In some implementations, each user 104, 106 customizes the global Neural Graphical Model by using the private clinical trial data 14, 16 of each user 104, 106 to create a personalized global Neural Graphical Model personalized to each individual user 104, 106. The private clinical trial data 14, 16 of each user 104, 106 may have different distributions and/or different feature sets. In some implementations, the users 104, 106 run an algorithm to incorporate client specific features from the private clinical trial data 14, 16 to create the personalized global Neural Graphical Model.

Figure 2:
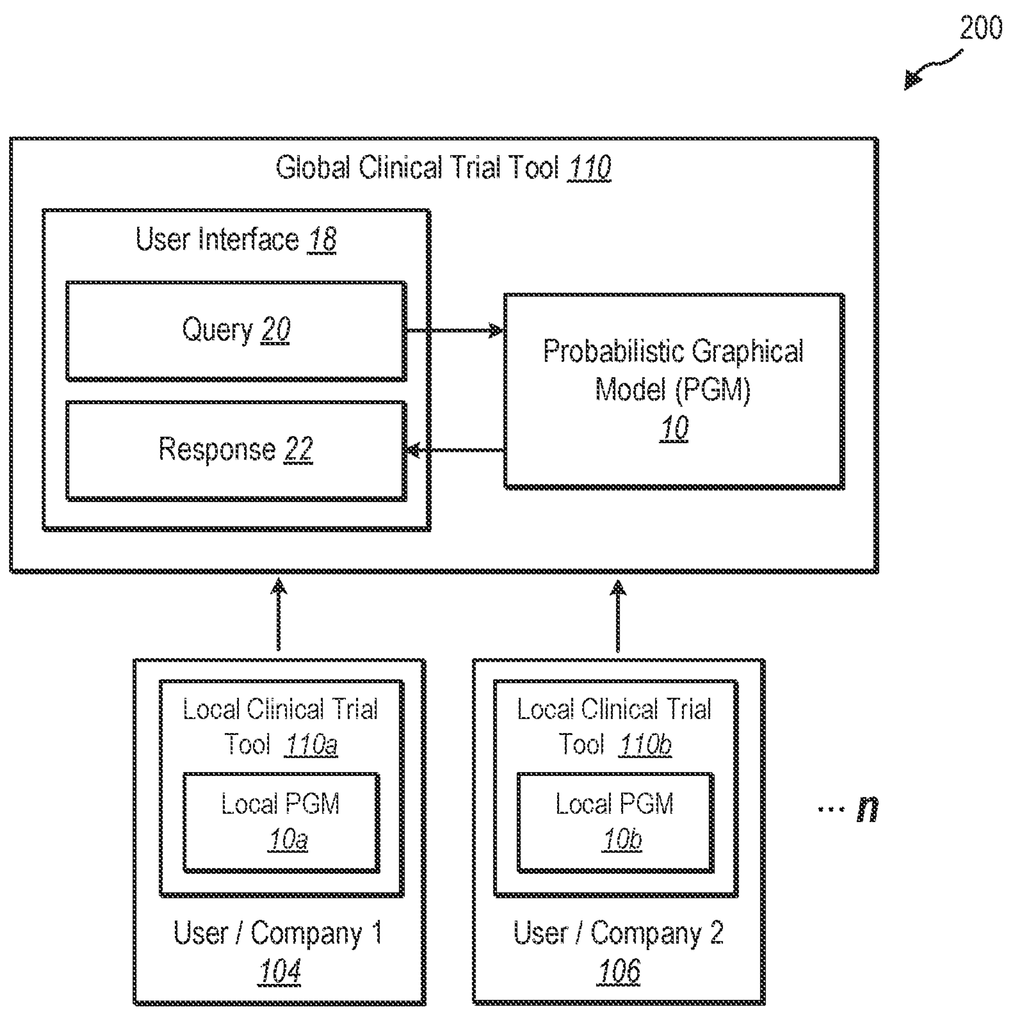
FIG. 2 illustrates an example environment for querying and analysis of clinical trials using probabilistic graphical models in accordance with implementations of the present disclosure.

FIG. 2 illustrates an example environment 200 for querying and analysis of clinical trials using probabilistic graphical models 10. The environment 200 includes a clinical trial tool 110 that one or more users 104, 106 access that aid the users 104, 106 in designing new clinical trials. The clinical trial tool 110 consists of a machine learning model and a user interface 18 with a query builder that allows the user to query the machine learning model (the probabilistic graphical model 10) and interact with the machine learning model (the probabilistic graphical model 10). In some implementations, the machine learning model is a Neural Graphical Model. The user interface 18 also includes a response presenter that provides a response 22 to the query 20.

The users 104, 106 access the clinical trial tool 110 using a computing device. In some implementations, the clinical trial tool 110 is a global clinical tool that is publicly accessible (or accessible to all users 104, 106) and uses a public probabilistic graphical model 10 trained on public clinical trial data 12 (FIG. 1) or a global Neural Graphical Model trained using federated learning. In some implementations, the clinical trial tool 110 is local to computing devices of the users 104, 106. For example, a local clinical trial tool 110*a* is local to a computing environment of the user 104 and uses a local probabilistic graphical model 10*a* trained using the private clinical data 14 (FIG. 1) of the user 104 and/or a combination of the private clinical data 14 and the public clinical trial data 12. Another example includes a local clinical trial tool 110*b* that is local to a computing environment of the user 106 and uses a local probabilistic graphical model 10*b* trained using the private clinical trial data 16 (FIG. 1) of the user 106 and/or a combination of the private clinical trial data 16 and the public clinical trial data 12. In some implementations, the clinical trial tool 110 is on a server (e.g., a cloud server) remote from the computing devices the users. In some implementations, the clinical trial tool 110 is hosted on virtual machines in the cloud. In some implementations, the clinical trial tool 110 is on an edge device. The clinical trial tool 110 aids the users 104, 106 in designing new clinical trials. For example, the new clinical trial is for a new treatment. Another example includes the new clinical trial is for a new drug to treat a disease.

The users 104, 106 provide queries 20 to the clinical trial tool 110 using the query builder of the user interface 18 and the clinical trial tool 110 outputs responses 22 to the queries 20 using the response presenter of the user interface 18. The queries 20 include any question the users 104, 106 ask relating to designing new clinical trials. In some implementations, the queries 20 are related to existing clinical trials. In some implementations, the queries 20 are queries of the users 104, 106 (e.g., researchers) for different fields related to a description of clinical trial study. For example, the queries 20 include questions regarding inclusion criteria for the new clinical trial (e.g., whether lowering the age criterion for inclusion would change the probability distribution over the variable representing successful recruitment in trial). Another example includes a query 20 asking how many clinics should participate in the new clinical trial to maximize the chance of successful recruitment while staying within a budget. Another example includes a query 20 asking whether a proposed evaluation protocol will result in volunteers dropping out of the trial.

In some implementations, the clinical trial tool 110 uses the probabilistic graphical model 10 to provide responses 22 to the queries 20. The probabilistic graphical model 10 allows the users 104, 106 to query over multiple variables in the domain. Moreover, since the probabilistic graphical model 10 learns the probability distribution of the clinical trial data (the public clinical trial data 12 and/or the private clinical trial data 14, 16) over the domain, the probabilistic graphical model 10 may be used to perform inference over any variable(s) without needing a separate predictive model for each variable. For example, the user 106 provides different values for the exclusion criteria and inclusion criteria for a new clinical trial in a query 20 to the clinical trial tool 110 and the clinical trial tool 110 uses the probabilistic graphical model 10 to provide a response 22 with a probability distribution over the new clinical trial completing and all other variables given the provided values for the exclusion criteria and the inclusion criteria.

The probabilistic graphical model 10 also allows the users 104, 106 to perform inference over variable(s) of interest. For example, the user 104 performs counterfactual reasoning for the new clinical trial by identifying different variables of interest for the new clinical trial in a query 20 to the clinical trial tool 110 and the clinical trial tool 110 uses the probabilistic graphical model 10 to provide a response 22 with maximum a posteriori values for the attributes of the new clinical trial most likely to achieve the variables of interest values provided by the user 104 in the query 20. The inference task may support any input data type and/or multimodal data using the probabilistic graphical model 10.

In some implementations, the clinical trial tool 110 uses a Neural Graphical Model to provide responses 22 to the queries 20. For example, the user 104 provides a query 20 to the clinical trial tool 110 for a new clinical trial or existing clinical trial and the clinical trial tool 110 uses the Neural Graphical Model to perform the inference task and provides a response 22 to the query 20. The query 20 may include observed or hypothetical evidence (assignment of values) on a subset of attributes of the new clinical trial or existing clinical trial. The response 22 to the query 20 will include conditional probability distribution over the remaining attributes of the new clinical trial or maximum a posteriori (MAP) assignment of values to the remaining attributes of the new clinical trial. The inference task may support any input data type and/or multimodal data using the Neural Graphical Model.

In some implementations, the clinical trial tool 110 uses for each user 104, 106 a personalized global Neural Graphical Model to perform inference tasks or sampling tasks for the new clinical trial or existing clinical trial. The clinical trial tool 110 can use any of the models (the probabilistic graphical model 10, a client-specific Neural Graphical Model, a global Neural Graphical Model, or the personalized global Neural Graphical Model) depending on the inference task. For example, clinical trial tool 110 performs one or more inference tasks on the global Neural Graphical Model in responding to the queries 20 of the users 104, 106. Another example includes a local clinical trial tool 110*a* running within the user 104 environment performs one or more inference tasks on the personalized global Neural Graphical Model for the user 104 in responding to queries 20 for the user's 104 new clinical trial or existing clinical trial. Another example includes a local clinical trial tool 110*b* running within user 106 environment performs one or more inference tasks on the personalized global Neural Graphical Model for the user 106 in responding to queries 20 for the user's 106 new clinical trial. Inference is the process of using the probabilistic graphical model 10 to answer the queries 20.

The inference task may support any input data type using the probabilistic graphical model 10. The probabilistic graphical model 10 generates predictions of any variable of interest, including overall success of the clinical trial, successful recruitment of volunteers, assess the probability of treatment being effective, etc. In addition, the probabilistic graphical model 10 may also provide insight into dependencies between variables in the clinical trial, providing the users 104, 106 with more reasoning capabilities for the client trials.

The users 104, 106 may repeatedly provide queries 20 to the clinical trial tool 110 to understand how changes to different attributes of the new clinical trial may affect the outcomes of the new clinical trial. The clinical trial tool 110 aids the users 104, 106 in creating better clinical trial designs for the new clinical trials that are cost effective and efficient.

In some implementations, one or more computing devices (e.g., servers and/or devices) are used to perform the processing of the environments 100 (FIG. 1) and 200. The one or more computing devices may include, but are not limited to, server devices, cloud virtual machines, personal computers, a mobile device, such as, a mobile telephone, a smartphone, a PDA, a tablet, or a laptop, and/or a non-mobile device. The features and functionalities discussed herein in connection with the various systems may be implemented on one computing device or across multiple computing devices. For example, the model training tool 102, the clinical trial tool 110 and the datastores 108 are implemented wholly on a computing device. Another example includes one or more subcomponents of the model training tool 102, the clinical trial tool 110 and/or the datastores 108 implemented across multiple computing devices. Moreover, in some implementations, one or more subcomponent of the model training tool 102, the clinical trial tool 110 and/or the datastores 108 may be implemented are processed on different server devices of the same or different cloud computing networks.

In some implementations, each of the components of the environments 100 and 200 is in communication with each other using any suitable communication technologies. In addition, while the components of the environments 100 and 200 are shown to be separate, any of the components or subcomponents may be combined into fewer components, such as into a single component, or divided into more components as may serve a particular implementation. In some implementations, the components of the environments 100 and 200 include hardware, software, or both. For example, the components of the environments 100 and 200 may include one or more instructions stored on a computer-readable storage medium and executable by processors of one or more computing devices. When executed by the one or more processors, the computer-executable instructions of one or more computing devices can perform one or more methods described herein. In some implementations, the components of the environment 100 include hardware, such as a special purpose processing device to perform a certain function or group of functions. In some implementations, the components of the environment 100 include a combination of computer-executable instructions and hardware.

Figure 3:
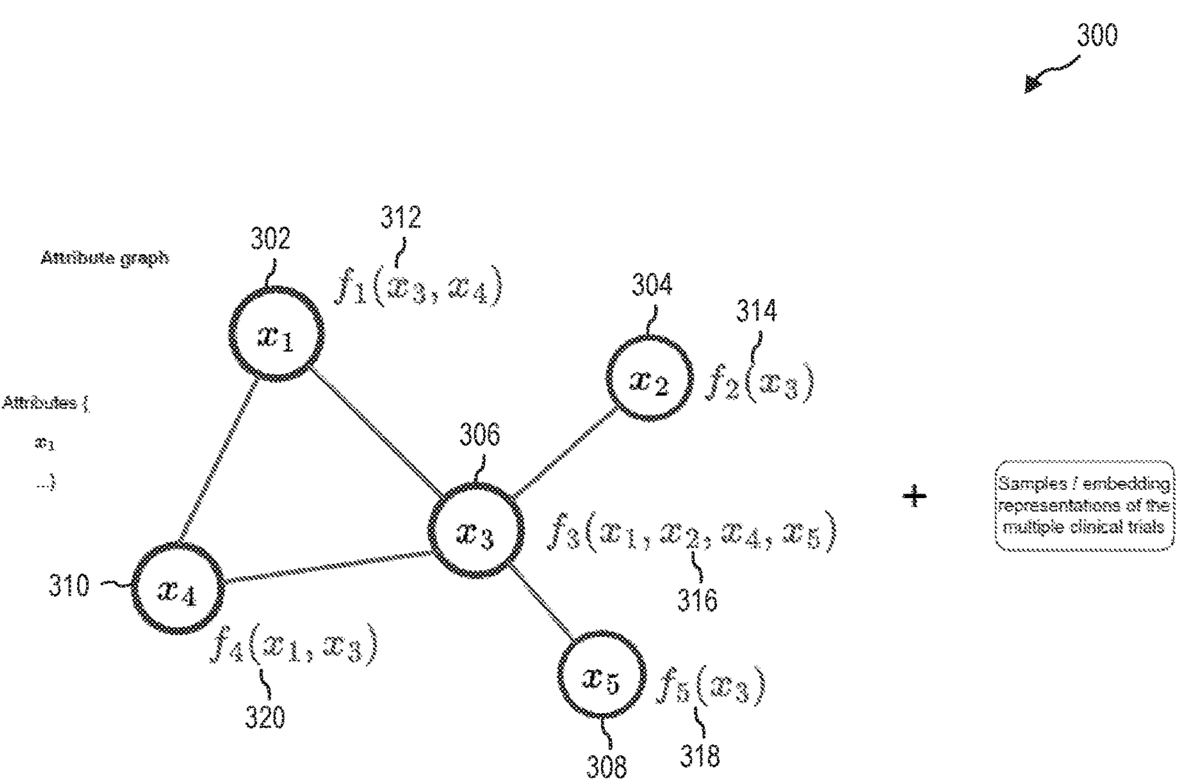
FIG. 3 illustrates an example attribute graph in accordance with implementations of the present disclosure.

FIG. 3 illustrates an example attribute graph 300 for clinical trials. In some implementations, the attribute graph 300 is provided to the model training tool 102 (FIG. 1) by a user. In some implementations, the attribute graph 300 is automatically learned by the model training tool 102. For example, the model training tool 102 uses the clinical trial graphs of the plurality of clinical trials to train the probabilistic graphical model 10.

The attribute graph 300 includes a plurality of nodes 302, 304, 306, 308, 310 that represent different attributes of clinical trials. The node 302 is for attribute $x_1$ of a clinical trial (e.g., a number of participants in the clinical trial). The node 304 is for attribute $x_2$ of a clinical trial (e.g., dosage requirements). The node 306 is for attribute $x_3$ of a clinical trial (e.g., inclusion criteria). The node 308 is for attribute $x_5$ of a clinical trial (e.g., exclusion criteria). The node 310 is for attribute $x_4$ of a clinical trial (e.g., clinic locations).

The attribute graph 300 includes a plurality of functions 312, 314, 316, 318, 320 that represent which nodes are a function of each other. The edges between the nodes 302, 304, 306, 308, 310 identify attributes of the clinical trials that have direct dependencies on one another. For example, the value of the node 302 for attribute $x_1$ is a function of values of the attributes $x_3$ and $x_4$. There is an edge between the node 302 and the node 306 and an edge between the node 302 and the node 310. The value of the node 304 for attribute $x_2$ is a function of the value of the attribute $x_3$. There is an edge between the node 304 and the node 306. The value of the node 306 for attribute $x_3$ is a function of value of the attributes $x_1$, $x_2$, $x_3$, $x_4$, and $x_5$. There is an edge between the node 306 and the nodes 302, 304, 308, 310. The value of the node 308 for attribute $x_5$ is a function of the value of attribute $x_3$. There is an edge between the node 308 and the node 306. The value of the node 310 for attribute $x_4$ is a function of values of the attributes $x_1$ and $x_3$. There is an edge between the node 310 and the node 302 and an edge between the node 310 and the node 306.

The model training tool 102 trains the probabilistic graphical model 10 (FIG. 1) using the samples and embedding representations from multiple clinical trials obtained from the public clinical trial data 12 and/or the private clinical trial data 14, 16.

Figure 4:
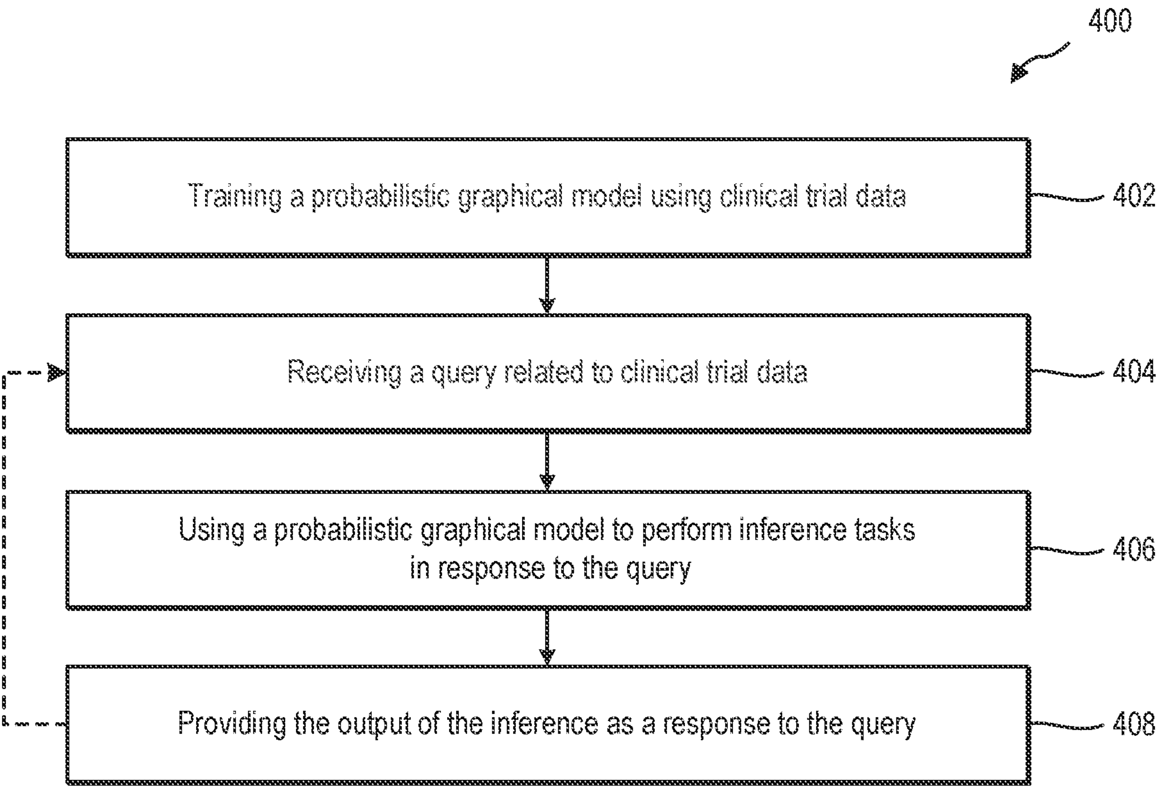
FIG. 4 illustrates an example method for using a probabilistic graphical model for obtaining queries from users and responding to queries for clinical trials in accordance with implementations of the present disclosure.

FIG. 4 illustrates an example method 400 for using a probabilistic graphical model 10 (FIGS. 1 and 2) for obtaining queries from users and responding to queries 20 (FIG. 2) for clinical trials. The actions of the method 400 are discussed below with reference to FIGS. 1-3.

At 402, the method 400 includes training a probabilistic graphical model using clinical trial data. The model training tool 102 trains the probabilistic graphical model 10 using clinical trial data. In some implementations, the clinical trial data is a combination of public clinical trial data 12 and private clinical trial data (e.g., private clinical trial data 14 or private clinical trial data 16). The probabilistic graphical model 10 represents a distribution over a domain of the clinical trial data.

In some implementations, the model training tool 102 trains the probabilistic graphical model 10 on data augmented with external data sources. The model training tool 102 uses a training algorithm that identifies which attributes in the clinical trial data (e.g., the public clinical trial data 12 and the private clinical trial data 14, 16) are directly dependent on each other and which pairs of attributes in the clinical trial data exhibit conditional independencies given other features. In some implementations, the probabilistic graphical model 10 has nodes representing different attributes of the clinical trial data and edges representing dependencies between the attributes.

In some implementations, the model training tool 102 trains the probabilistic graphical model 10 using public clinical trial data 12. The model training tool 102 uses a structure of clinical trial data in training the probabilistic graphical model 10 using the clinical trial data. The clinical trial data is structured in a specific format and the model training tool 102 uses the specific format in training the probabilistic graphical model 10 and using augmented data conformed to the specific format in the training of the probabilistic graphical model 10. In some implementations, the model training tool 102 automatically creates an attribute graph 300 for the clinical trial data using the structure of the clinical trial data. In some implementations, the model training tool 102 discovers the attribute graph 300 for the clinical trial data. In some implementations, the model training tool 102 receives an attribute graph 300 created for the for the clinical trial data using the structure of the clinical trial data.

In some implementations, the probabilistic graphical model 10 trained on the clinical trial data is a Neural Graphical Model with nodes representing different attributes of the clinical trial data and encodes a distribution over a domain of the clinical trial data using a deep neural network. The Neural Graphical Model 26 represents a probability function over the domain.

In some implementations, the model training tool 102 trains the Neural Graphical Model based on a plurality of private clinical trial datasets (e.g., the private clinical trial data 14 and the private clinical trial data 16) using a federated learning framework. The federated learning framework pools the knowledge from models trained on private clinical trial data from a plurality of users without access to private clinical trial data (e.g., the private clinical data 14 of the users 104 and the private clinical trial data 16 for the user 106) to obtain more accurate assessment of clinical trial success rates for each phase and provide insight into features with most impact on that success and provide more accurate models for everyone to use in the inference and sampling tasks for clinical trials.

At 404, the method 400 includes receiving a query for a new clinical trial. The clinical trial tool 110 receives a query 20 for a new clinical trial. In some implementations, the query 20 is for an existing clinical trial. For example, the clinical trial tool 110 receive a query 20 from a user 104. In some implementations, the clinical trial tool 110 is a global clinical tool that is publicly accessible (or accessible to all users 104, 106) and uses a public probabilistic graphical model 10 trained on public clinical trial data 12 or a global Neural Graphical Model trained using federated learning in responding to the query 20.

In some implementations, the clinical trial tool 110 is local to computing devices of the users 104, 106. For example, a local clinical trial tool 110*a* is local to a computing environment of the user 104 and uses a local probabilistic graphical model 10*a* trained using the private clinical data 14 of the user 104 and/or a combination of the private clinical data 14 and the public clinical trial data 12 in responding to the query 20. Another example includes a local clinical trial tool 110*b* that is local to a computing environment of the user 106 and uses a local probabilistic graphical model 10*b* trained using the private clinical trial data 16 of the user 106 and/or a combination of the private clinical trial data 16 and the public clinical trial data 12 in responding to the query 20.

In some implementations, the query 20 includes attributes and values for the attributes for designing a new clinical trial or analyzing an existing trial. In some implementations, the query 20 includes a variable of interest for the new clinical trial or an existing clinical trial. In some implementations, the query 20 includes a plurality of variables of interest for the new clinical trial or an existing clinical trial.

At 406, the method 400 includes using the probabilistic graphical model to perform inference tasks in response to the query. The clinical trial tool 110 uses the probabilistic graphical model 10 to perform inference tasks in response to the query 20 and provide the response 22 to the query 20. In some implementations, the clinical trial tool 110 uses the Neural Graphical Model to perform the inference tasks in response to the query 20 and provide the response 22 to the query 20.

The inference task may support any input data type using the probabilistic graphical model 10. The probabilistic graphical model 10 generates predictions of any variable of interest, including overall success of the clinical trial, successful recruitment of volunteers, assessment of the probability of treatment being effective, etc. In addition, the probabilistic graphical model 10 may also provide insight into dependencies between variables in the clinical trial, providing the users 104, 106 with more reasoning capabilities for the client trials.

The probabilistic graphical model 10 also allows the users 104, 106 to perform inference over the variable(s) of interest. For example, the user 104 performs counterfactual reasoning for the new clinical trial by identifying different variables of interest for the new clinical trial in a query 20 to the clinical trial tool 110 and the clinical trial tool 110 uses the probabilistic graphical model 10 to provide a response 22 with values for the remaining attributes of the new clinical trial most likely to achieve a given specific value of the variables of interest provided by the user 104.

At 408, the method 400 includes providing the output of the inference tasks as a response to the query. The clinical trial tool 110 provides the output of the inference tasks as a response 22 to the query 20. In some implementations, the response 22 is a probability distribution over the remaining attributes conditioned on the values of the attributes provided in the query 20.

In some implementations, the response 22 includes a maximum a posteriori (MAP) assignment of values for the remaining attributes given specific values of the variable of interest in the query 20. In some implementations, the response 22 includes an assignment of a maximum a posteriori (MAP) values to the remaining attributes of the new clinical trial or an existing clinical trial to most likely to achieve the specific values for plurality of outcome variables in the query 20.

As a new query 20 is received, the method 400 returns to 404 and the clinical trial tool 110 uses the probabilistic graphical model 10 to provide a response 22 to the new query 20. The users 104, 106 may repeatedly provide queries 20 to the clinical trial tool 110 to understand how changes to values of different attributes of the new clinical trial may affect the outcomes or other attributes of the new clinical trial. The method 400 aids the users 104, 106 in creating better clinical trial designs for the new clinical trials that are cost effective and efficient.

Figure 5:
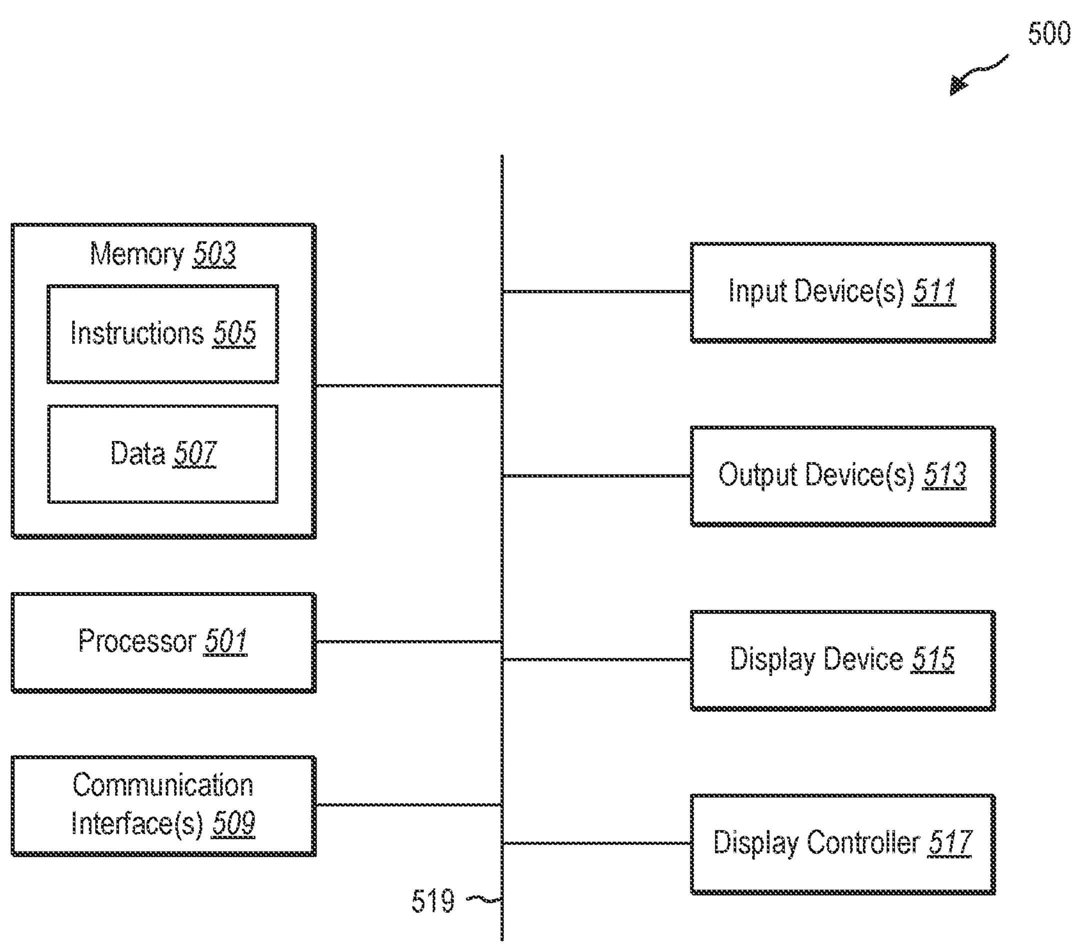
FIG. 5 illustrates components that may be included within a computer system.

FIG. 5 illustrates components that may be included within a computer system 500. One or more computer systems 500 may be used to implement the various methods, devices, components, and/or systems described herein.

The computer system 500 includes a processor 501. The processor 501 may be a general-purpose single or multi-chip microprocessor (e.g., an Advanced RISC (Reduced Instruction Set Computer) Machine (ARM)), a special purpose microprocessor (e.g., a digital signal processor (DSP)), a graphics processing unit (GPU), a microcontroller, a programmable gate array, etc. The processor 501 may be referred to as a central processing unit (CPU). Although just a single processor 501 is shown in the computer system 500 of FIG. 5, in an alternative configuration, a combination of processors (e.g., an ARM and DSP) could be used.

The computer system 500 also includes memory 503 in electronic communication with the processor 501. The memory 503 may be any electronic component capable of storing electronic information. For example, the memory 503 may be embodied as random access memory (RAM), read-only memory (ROM), magnetic disk storage mediums, optical storage mediums, flash memory devices in RAM, on-board memory included with the processor, erasable programmable read-only memory (EPROM), electrically erasable programmable read-only memory (EEPROM) memory, registers, and so forth, including combinations thereof.

Instructions 505 and data 507 may be stored in the memory 503. The instructions 505 may be executable by the processor 501 to implement some or all of the functionality disclosed herein. Executing the instructions 505 may involve the use of the data 507 that is stored in the memory 503. Any of the various examples of modules and components described herein may be implemented, partially or wholly, as instructions 505 stored in memory 503 and executed by the processor 501. Any of the various examples of data described herein may be among the data 507 that is stored in memory 503 and used during execution of the instructions 505 by the processor 501.

A computer system 500 may also include one or more communication interfaces 509 for communicating with other electronic devices. The communication interface(s) 509 may be based on wired communication technology, wireless communication technology, or both. Some examples of communication interfaces 509 include a Universal Serial Bus (USB), an Ethernet adapter, a wireless adapter that operates in accordance with an Institute of Electrical and Electronics Engineers (IEEE) 802.11 wireless communication protocol, a Bluetooth® wireless communication adapter, and an infrared (IR) communication port.

A computer system 500 may also include one or more input devices 511 and one or more output devices 513. Some examples of input devices 511 include a keyboard, mouse, microphone, remote control device, button, joystick, trackball, touchpad, and lightpen. Some examples of output devices 513 include a speaker and a printer. One specific type of output device that is typically included in a computer system 500 is a display device 515. Display devices 515 used with embodiments disclosed herein may utilize any suitable image projection technology, such as liquid crystal display (LCD), light-emitting diode (LED), gas plasma, electroluminescence, or the like. A display controller 517 may also be provided, for converting data 507 stored in the memory 503 into text, graphics, and/or moving images (as appropriate) shown on the display device 515.

The various components of the computer system 500 may be coupled together by one or more buses, which may include a power bus, a control signal bus, a status signal bus, a data bus, etc. For the sake of clarity, the various buses are illustrated in FIG. 5 as a bus system 519.

In some implementations, the various components of the computer system 500 are implemented as one device. For example, the various components of the computer system 500 are implemented in a mobile phone or tablet. Another example includes the various components of the computer system 500 implemented in a personal computer. Another example includes the various components of the computer system 500 implemented in the cloud. Another example includes the various components of the computer system 500 implemented on an edge device.

As illustrated in the foregoing discussion, the present disclosure utilizes a variety of terms to describe features and advantages of the model evaluation system. Additional detail is now provided regarding the meaning of such terms. For example, as used herein, a "machine learning model" refers to a computer algorithm or model (e.g., a classification model, a clustering model, a regression model, a language model, an object detection model, a probabilistic graphical model) that can be tuned (e.g., trained) based on training input to approximate unknown functions. For example, a machine learning model may refer to a neural network (e.g., a convolutional neural network (CNN), deep neural network (DNN), recurrent neural network (RNN)), or other machine learning algorithm or architecture that learns and approximates complex functions and generates outputs based on a plurality of inputs provided to the machine learning model. As used herein, a "machine learning system" may refer to one or multiple machine learning models that cooperatively generate one or more outputs based on corresponding inputs. For example, a machine learning system may refer to any system architecture having multiple discrete machine learning components that consider different kinds of information or inputs.

The techniques described herein may be implemented in hardware, software, firmware, or any combination thereof, unless specifically described as being implemented in a specific manner. Any features described as modules, components, or the like may also be implemented together in an integrated logic device or separately as discrete but interoperable logic devices. If implemented in software, the techniques may be realized at least in part by a non-transitory processor-readable storage medium comprising instructions that, when executed by at least one processor, perform one or more of the methods described herein. The instructions may be organized into routines, programs, objects, components, data structures, etc., which may perform particular tasks and/or implement particular data types, and which may be combined or distributed as desired in various implementations.

Computer-readable mediums may be any available media that can be accessed by a general purpose or special purpose computer system. Computer-readable mediums that store computer-executable instructions are non-transitory computer-readable storage media (devices). Computer-readable mediums that carry computer-executable instructions are transmission media. Thus, by way of example, and not limitation, implementations of the disclosure can comprise at least two distinctly different kinds of computer-readable mediums: non-transitory computer-readable storage media (devices) and transmission media.

As used herein, non-transitory computer-readable storage mediums (devices) may include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

The steps and/or actions of the methods described herein may be interchanged with one another without departing from the scope of the claims. In other words, unless a specific order of steps or actions is required for proper operation of the method that is being described, the order and/or use of specific steps and/or actions may be modified without departing from the scope of the claims.

The term "determining" encompasses a wide variety of actions and, therefore, "determining" can include calculating, computing, processing, deriving, investigating, looking up (e.g., looking up in a table, a database, a datastore, or another data structure), ascertaining and the like. Also, "determining" can include receiving (e.g., receiving information), accessing (e.g., accessing data in a memory) and the like. Also, "determining" can include resolving, selecting, choosing, establishing, predicting, inferring, and the like.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one implementation" or "an implementation" of the present disclosure are not intended to be interpreted as excluding the existence of additional implementations that also incorporate the recited features. For example, any element described in relation to an implementation herein may be combinable with any element of any other implementation described herein. Numbers, percentages, ratios, or other values stated herein are intended to include that value, and also other values that are "about" or "approximately" the stated value, as would be appreciated by one of ordinary skill in the art encompassed by implementations of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to implementations disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the implementations that falls within the meaning and scope of the claims is to be embraced by the claims.

The present disclosure may be embodied in other specific forms without departing from its spirit or characteristics. The described implementations are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method, comprising:

training a probabilistic graphical model using clinical trial data using a federated learning framework that learns an underlying data distributions from the clinical trial data, wherein the probabilistic graphical model is a graphical model with nodes representing different attributes of the clinical trial data and encoding a distribution over a domain of the clinical trial data using a deep neural network;

receiving, via a user interface, a query for a new clinical trial, wherein the user interface aids a user in interacting with the probabilistic graphical model;

using the probabilistic graphical model to perform inference tasks in response to the query; and providing, on the user interface, an output of the inference tasks as a response to the query.

2. The method of claim 1, wherein training the probabilistic graphical model further includes training the probabilistic graphical model on data augmented with external data sources.

3. The method of claim 1, wherein training the probabilistic graphical model further includes identifying which attributes in the clinical trial data are directly dependent on each other or which pairs of attributes in the clinical trial data exhibit conditional independencies given other features.

4. The method of claim 1, wherein training the probabilistic graphical model uses an attribute graph to train the probabilistic graphical model over the clinical trial data, wherein the attribute graph is discovered or provided by experts.

5. The method of claim 1, wherein the clinical trial data is structured in a specific format and training the probabilistic graphical model includes training the probabilistic graphical model on the structure of the specific format and using augmented data conformed to the specific format in training the probabilistic graphical model.

6. The method of claim 1, wherein the clinical trial data is a combination of public clinical trial data and private clinical trial data.

7. The method of claim 1, wherein training the probabilistic graphical model occurs using a global model training tool that uses public clinical trial data to train the probabilistic graphical model, and wherein the probabilistic graphical model is available to a plurality of users to perform inference tasks in response to queries received from the plurality of users.

8. The method of claim 1, wherein training the probabilistic graphical model occurs using a local model training tool of a user that uses a combination of private clinical trial data of the user and public clinical trial data to train the probabilistic graphical model, and wherein the probabilistic graphical model is available to the user to perform the inference tasks in response to queries received from the user.

9. The method of claim 1, wherein the query includes attributes and values for corresponding attributes for designing the new clinical trial or analyzing an existing clinical trial and the response is a probability distribution over the values of remaining attributes conditioned on the values of the attributes provided in the query.

10. The method of claim 1, wherein the query includes a variable of interest for the new clinical trial or existing clinical trial and the response includes a maximum a posteriori (MAP) assignment of values for remaining attributes given specific values of the variable of interest.

11. The method of claim 1, wherein the query includes a plurality of variables of interest for the new clinical trial or existing clinical trial and the response includes an assignment of a maximum a posteriori (MAP) values to remaining attributes of the new clinical trial or the existing clinical trial to achieve specified values for a plurality of outcome variables.

12. A device, comprising:

a memory to store data and instructions; and a processor operable to communicate with the memory, wherein the processor is operable to:

train a probabilistic graphical model using clinical trial data using a federated learning framework that learns an underlying data distributions from the clinical trial data, wherein the probabilistic graphical model is a graphical model with nodes representing different attributes of the clinical trial data and encoding a distribution over a domain of the clinical trial data using a deep neural network;

receive, via a user interface, a query for a new clinical trial, wherein the user interface aids a user in interacting with the probabilistic graphical model;

use the probabilistic graphical model to perform inference tasks in response to the query; and provide, on the user interface, an output of the inference tasks as a response to the query.

13. The device of claim 12, wherein the processor is further operable to train the probabilistic graphical model using a combination of public clinical trial data and private clinical trial data.

14. The device of claim 12, wherein the processor is further operable to train the probabilistic graphical model on data augmented with external data sources.

15. The device of claim 12, wherein the processor is further operable to train the probabilistic graphical model by identifying which attributes in the clinical trial data are directly dependent on each other and which pairs of attributes in the clinical trial data exhibit conditional independencies given other features.

16. The device of claim 12, wherein the query includes attributes and values for the attributes for designing a new clinical trial or analyzing an existing clinical trial and the response is a probability distribution over remaining attributes conditioned on the values of the attributes provided in the query.

17. The device of claim 12, wherein the query includes a variable of interest for the new clinical trial or existing clinical trial and the response includes a maximum a posteriori (MAP) assignment of values for remaining attributes given specific values of the variable of interest.

18. The device of claim 12, wherein the query includes a plurality of variables of interest for the new clinical trial or an existing clinical trial and the response includes an assignment of a maximum a posteriori (MAP) values to remaining attributes of the new clinical trial or the existing clinical trial to achieve specified values of the plurality of variables of interest.

* * * * *